(12) United States Patent
Nazareth et al.

(10) Patent No.: US 9,939,385 B2
(45) Date of Patent: Apr. 10, 2018

(54) SYSTEMS, METHODS, AND TEST KITS FOR ANALYTE VARIATION DETECTION

(75) Inventors: Albert Nazareth, Mercerville, NJ (US);
Andy Sturman, San Diego, CA (US);
Benedict Zin, San Diego, CA (US);
Yea-Shun Cheng, Doylestown, PA (US); Henry Bell, Hamilton Square, NJ (US); Shang Li, West Windsor, NJ (US)

(73) Assignee: Church & Dwight Co., Inc., Princeton, NJ (US)

( * ) Notice: Subject to any disclaimer, the term of this patent is extended or adjusted under 35 U.S.C. 154(b) by 0 days.

(21) Appl. No.: 13/229,156

(22) Filed: Sep. 9, 2011

(65) Prior Publication Data

US 2013/0065321 A1 Mar. 14, 2013

(51) Int. Cl.
*G01N 21/84* (2006.01)

(52) U.S. Cl.
CPC ................................ *G01N 21/8483* (2013.01)

(58) Field of Classification Search
CPC ........................... G01N 21/78; G01N 21/8483
USPC ........................... 436/65, 500, 814, 817, 906
See application file for complete search history.

(56) References Cited

U.S. PATENT DOCUMENTS

| | | | |
|---|---|---|---|
| 5,467,778 A | 11/1995 | Catt et al. | |
| 5,657,762 A | 8/1997 | Coley et al. | |
| 5,786,220 A * | 7/1998 | Pronovost et al. | 436/518 |
| 6,146,333 A | 11/2000 | Mcneirney et al. | |
| 6,234,974 B1 | 5/2001 | Catt et al. | |
| 6,364,844 B1 | 4/2002 | Regas et al. | |
| 6,451,619 B1 * | 9/2002 | Catt et al. | 436/514 |
| 6,454,726 B1 | 9/2002 | Catt et al. | |
| 6,585,663 B1 | 7/2003 | Coley et al. | |
| 6,927,064 B1 | 8/2005 | Catt et al. | |
| 7,039,561 B2 * | 5/2006 | Wei | 702/191 |
| 7,044,919 B1 | 5/2006 | Catt et al. | |
| 7,090,802 B1 * | 8/2006 | Wang et al. | 422/417 |
| 7,534,393 B2 | 5/2009 | Catt et al. | |
| 2002/0068358 A1 * | 6/2002 | Campbell et al. | 435/289.1 |
| 2004/0063219 A1 * | 4/2004 | Bateman et al. | 436/514 |
| 2008/0103447 A1 * | 5/2008 | Reggiardo et al. | 604/131 |
| 2010/0172802 A1 | 7/2010 | Sharrock et al. | |
| 2010/0280811 A1 * | 11/2010 | Gorenstein | G01N 30/8624 703/12 |

FOREIGN PATENT DOCUMENTS

WO WO 95/16920 * 6/1995

OTHER PUBLICATIONS

Adlercreutz et al. "The measurement of urinary steroid glucuronides as indices of the fertile period in women." J. Steroid Biochem. 17(6):695-702 (1982).

(Continued)

*Primary Examiner* — Melanie Yu Brown
(74) *Attorney, Agent, or Firm* — Church & Dwight Co., Inc.

(57) ABSTRACT

Systems, methods, and test kits for monitoring and detecting variation in an analyte level in a fluid sample from an individual variation using a uniquely determined analyte threshold value. In one implementation, luteinizing hormone is the monitored analyte and is compared with the determined threshold value to predict the onset of ovulation for the individual.

18 Claims, 8 Drawing Sheets

(56) References Cited

OTHER PUBLICATIONS

Clearblue® easy Fertility Monitor Instruction Booklet.
Gougeon et al. "Age-related changes of the population of human ovarian follicles: increase in the disappearance rate of non-growing and early-growing follicles in aging women." Biol. Reprod. 50(3):653-663 (1994).
Pearlstone et al. "Ovulation induction in women age 40 and older: the importance of basal follicle-stimulating hormone level and chronological age." Fertil. Steril. 58(4): 674-679 (1992).
Stovall et al. "Serum progesterone and uterine curettage in differential diagnosis of ectopic pregnancy." Fertil. Steril. 57(2):456-457 (1992).
The Practice Committee of the American Society for Reproductive Medicine. "Aging and infertility in women." Fertil. Steril. 82(Suppl 1):S102-106 (2004).
Toner et al. "Basal follicle-stimulating hormone level is a better predictor of in vitro fertilization performance than age." Fertil. Steril. 55(4):784-791 (1991).
WHO. "Temporal relationships between indices of the fertile period." Fertil Steril. 39(5):647-655 (1983).

\* cited by examiner

SYSTEMS, METHODS, AND TEST KITS FOR ANALYTE VARIATION DETECTION

FIELD

The present invention relates to the field of analyte detection systems and methods, with particular applicability to predicting the timing of ovulation.

BACKGROUND

Analysis of the levels of hormone in an individual can provide important and helpful prognostic information. For example, detected hormone levels may enable an evaluation of a woman's health concerns such as fertility, pregnancy and menopause. One component in evaluating a woman's fertility status is assessing her ovulatory function. The average menstrual cycle generally lasts 28 days, during which there is a transition from the follicular phase to the luteal phase. The follicular phase of the menstrual cycle begins on the first day of menstruation and is followed by a rise in follicle-stimulating hormone (FSH), luteinizing hormone (LH) and estrogen, the latter promoting the maturation of a follicle. Once estrogen levels reach an optimal concentration and duration, the pituitary gland is prompted to release a large burst of LH secretion that significantly raises the concentration of circulating LH in blood. This rise in circulating hormone is known as LH surge. This surge in LH marks the transition to the luteal phase of the cycle, resulting in final maturation of the follicle, release of a mature oocyte from the follicle (ovulation), and corpus luteum formation. After ovulation, estrogen levels continue to rise along with an increase in progesterone levels in order to prepare the endometrium for implantation. If fertilization of the oocyte occurs, the implantation of the fertilized oocyte within the uterine endometrial lining triggers production of human chorionic gonadotropins (hCG) that maintains the corpus luteum and progesterone production. However in the absence of fertilization, the corpus luteum deteriorates resulting in a decrease in the levels of both estrogen and progesterone, and sloughing of the endometrial lining thereby marking the onset of the next cycle.

In assessing ovulatory function, daily measurements of LH levels may be used to predict the timing of ovulation. The rise in blood LH may occur ~24-36 hours prior to ovulation.

Measurements of serum progesterone levels 18 to 24 days after the onset of menses or seven days before the next cycle may be used to confirm whether ovulation had occurred. In the event of a confirmed pregnancy, serum progesterone levels may be utilized to assess nonviable pregnancies, e.g., ectopic pregnancy or spontaneous abortion (miscarriage). In pregnant individuals, a serum progesterone value of ≥25 ng/ml is 98% of the time associated with a viable pregnancy, while a value of <5 ng/ml identifies a nonviable pregnancy.

Another component in evaluating a woman's fertility status may be assessing the functioning potential of the ovary with respect to the quantity and quality of the oocytes within the ovary, commonly referred to as ovarian reserve. An acceleration of follicular loss is prevalent in the last 10-15 years before menopause. This loss correlates with a subtle increase in FSH. One test that may be used to assess ovarian reserve is the Day 3 FSH test. This test determines the level of FSH on cycle day three during which estrogen level is expected to be low. A cycle day three FSH level <10 IU/L is suggestive of adequate ovarian reserve, whereas an FSH level >25 IU/L is associated with a chance of pregnancy close to zero during ovulation induction.

A woman's fertility may also be affected by fluctuations in thyroid gland function. The measurement of thyroid-stimulating hormone (TSH) levels may be used as a screening test. Briefly, thyrotropin-releasing hormone (TRH) prompts the pituitary gland to produce TSH. However, THR also prompts the pituitary to release more of the hormone prolactin (PRL). Elevations of PRL can interfere with ovulation by suppressing release of the hormones LH and FSH, which stimulate the ovary. Low levels of TSH may also interfere with the rate of metabolism of sex hormones, which may also cause ovulatory disorders. Menstrual irregularities and bleeding problems are common in hypothyroid women.

Diagnostic tests for screening analytes, e.g. urinary hormones or metabolites thereof, may utilize antibodies specific to the analyte. A change in the level from a predetermined threshold level may be noted by differences in color or color intensity compared with the color in a reference window or a reference guide. The color change may be produced using techniques such as enzyme-linked immunosorbent assays or lateral flow color matching assays to indicate the amount of analyte in a urine sample.

Improvements to the diagnostic tests for fertility monitoring have been made by removing the step which required the individual to interpret the results. In these products, electronic sensors and displays provide clear outputs indicating analyte levels. For example, the Clearblue® Easy Fertility Monitor (CBEFM) provides a method for monitoring the fertility status of an individual using two hormones: LH and estrogen with electronic reading and a digital display. The Clearblue® Digital Ovulation Test (CDOT) is another commercially available device, which employs a variable threshold for LH surge determination, and is also an improvement over the color matching visually read tests. Although both CBEFM and CDOT show improvement over the art, there still remains a need for such diagnostic devices that are affordable to the average consumer and provide simplicity of use over the prior art. Accordingly, improvements in detection systems are desirable.

SUMMARY

The systems, methods, and devices of the disclosure each have several innovative aspects, no single one of which is solely responsible for the desirable attributes disclosed herein.

A method of detecting a variation in a monitored analyte level in a fluid sample from an individual is provided. The method includes collecting a series of samples over a single biological cycle of the individual, determining a baseline from a plurality of samples in the series, determining a threshold associated with the monitored analyte level for the individual based at least in part on the determined baseline, generating a signal representative of the monitored analyte level in one or more samples in the series, comparing the signal to the threshold, and generating an output based at least in part on a result of the comparing.

A device for detecting a variation in a monitored analyte level in a fluid sample from an individual is provided. The device includes means for collecting a series of samples, means for determining a baseline from a plurality of samples in the series, means for determining a threshold associated with the monitored analyte level for the individual based at least in part on the determined baseline, means for generating a signal representative of the monitored analyte level in one or more samples in the series, means for comparing the signal to the threshold, and means for generating an output signal in response to the means for comparing.

A test kit for detecting a variation in a monitored analyte level in a fluid sample from an individual is provided. The test kit includes fluid sample collectors and a reader. The reader includes a port for accepting a fluid sample collector therein and a circuit. The circuit may be configured to determine a baseline from a plurality of initial samples in a series of samples collected with a series of fluid sample collectors, determine a threshold associated with the monitored analyte level for the individual based at least in part on the determined baseline, generate a signal representative of the monitored analyte level in one or more samples in the series collected subsequent to the initial samples, compare the signal to the threshold, and generate an output signal based at least in part on the result of the comparing.

Details of one or more implementations of the subject matter described in this specification are set forth in the accompanying drawings and the description below. Other features, aspects, and advantages will become apparent from the description, drawings, and claims. Note that the relative dimensions of the following figures may not be drawn to scale.

DETAILED DESCRIPTION

For many people, having a child provides a life affirming achievement in one's life. Conceiving a child is not by any means an easy task. With the rise of expensive fertility clinics to assist in the conception process, the public demand for scientific methods to help begin their path to parenthood is evident. As a low cost alternative, home test kits have become available. However, these kits may require lengthy calibration periods. These kits may feature results display which is difficult to read and/or interpret. Furthermore, these kits, in an effort to simplify the test, may feature a "one-size-fits-all" assay which may not be appropriate for the body chemistry of all potential users of the kit.

In most cases, diagnostic devices rely on the individual's hormone level to be either "high" or "low" relative to a fixed threshold value. It has been found that many individual subjects do not conform to the average in terms of basal circulating hormone levels, cycle length and/or the duration of the cycle. Furthermore, variations can extend from one cycle to another in the same individual, making the use of a fixed threshold for the entire population problematic. In the CBEFM device mentioned above, the user will monitor their urine sample over multiple menstrual cycles. The monitor stores the data, compares readings day to day, and identifies the days of maximum fertility. Although the CBEFM includes some capability to learn from previous cycles, this feature cannot be effective for the first cycle. These drawbacks are resolved in the inventive embodiments described herein.

In one implementation, a test kit may include two units, a digital reader and a package that contains multiple disposable test sticks. Because the test method can be effective in a single cycle, the kit may include only enough disposable test sticks for a single cycle of tests, for example, about 20. The reader may be activated mechanically, more preferably, activation is achieved by the change of the light reflectance of the background with or without the test stick. The reader may also be designed to be activated by inserting a single-use disposable test stick and to measure the color development at the detection area of the test strip after a urine sample is applied. At the completion of the test, the test result may be converted to an electronic or digital output. The disposable test stick design may be based on lateral flow technology and contain a test strip with necessary reagents that allow for the detection of luteinizing hormone (LH), follicle stimulating hormone, human chorionic gonadotropin, estrogen, progesterone, testosterone, or metabolites thereof.

In an implementation for detecting LH surge, ovulation prediction may be achieved by establishing a basal LH level based at least in part on non-surge urine samples tested during the early phase of the cycle, followed by comparing the LH level of subsequent samples to a threshold derived at least in part from the basal LH level. In one such implementation, the LH surge may detected by detecting an elevated level of LH based on a threshold which is defined as three times the established basal LH levels for that individual. This threshold may be totally unique for each user and cycle, and may be based at least in part on her individual hormonal levels. With this technique, personalized threshold levels are established for each user and also for each cycle, improving accuracy and ease of use over existing products and methods.

Figure 1:
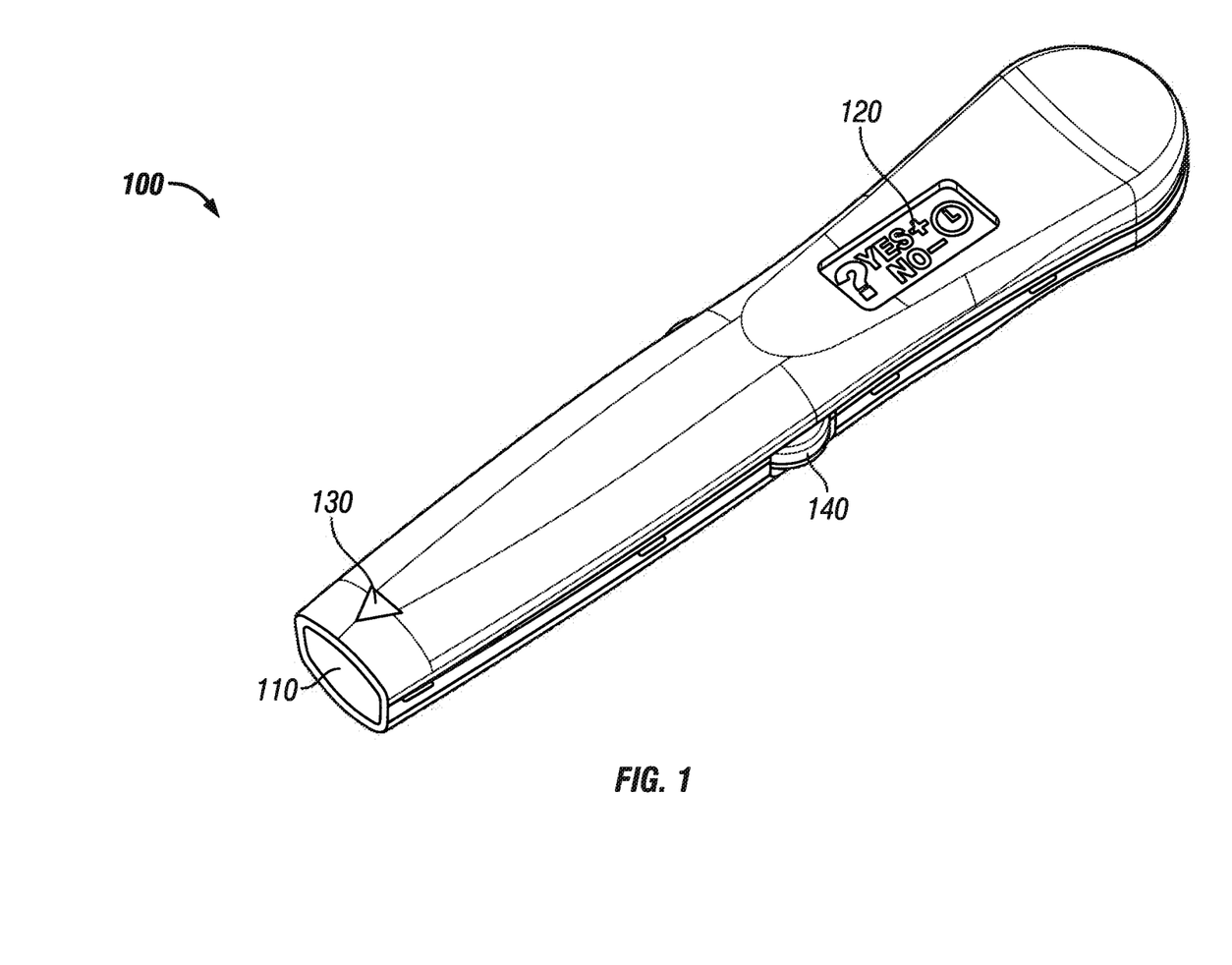
FIG. 1 is a top perspective view of an example of a reader device without a disposable test stick according to an implementation of the invention.

FIG. 1 is a top perspective view of a reader device of such a kit without a disposable test stick installed. A device 100 may be formed from plastic, metal, or other material. The device 100 includes a test stick acceptor port 110. The test strip acceptor port is designed to receive test sticks for analysis. The device 100 also includes a display 120. The display 120 may render various icons or messages to a user such as test results, device status, or error messages. The display 120 may be color or monochrome. In an example implementation, the display 120 may be a liquid crystal display (LCD). The device may further include a test stick alignment marker 130. In the example shown, the test strip alignment marker 130 is a triangle pointing to the test stick acceptor 110. The test stick alignment marker aids with insertion of a test stick into the device 100. The device 100 may include a test stick ejector 140. The test stick ejector 140 may be a manual or electronic mechanism to eject a previously inserted test stick from the device 100.

Figure 2:
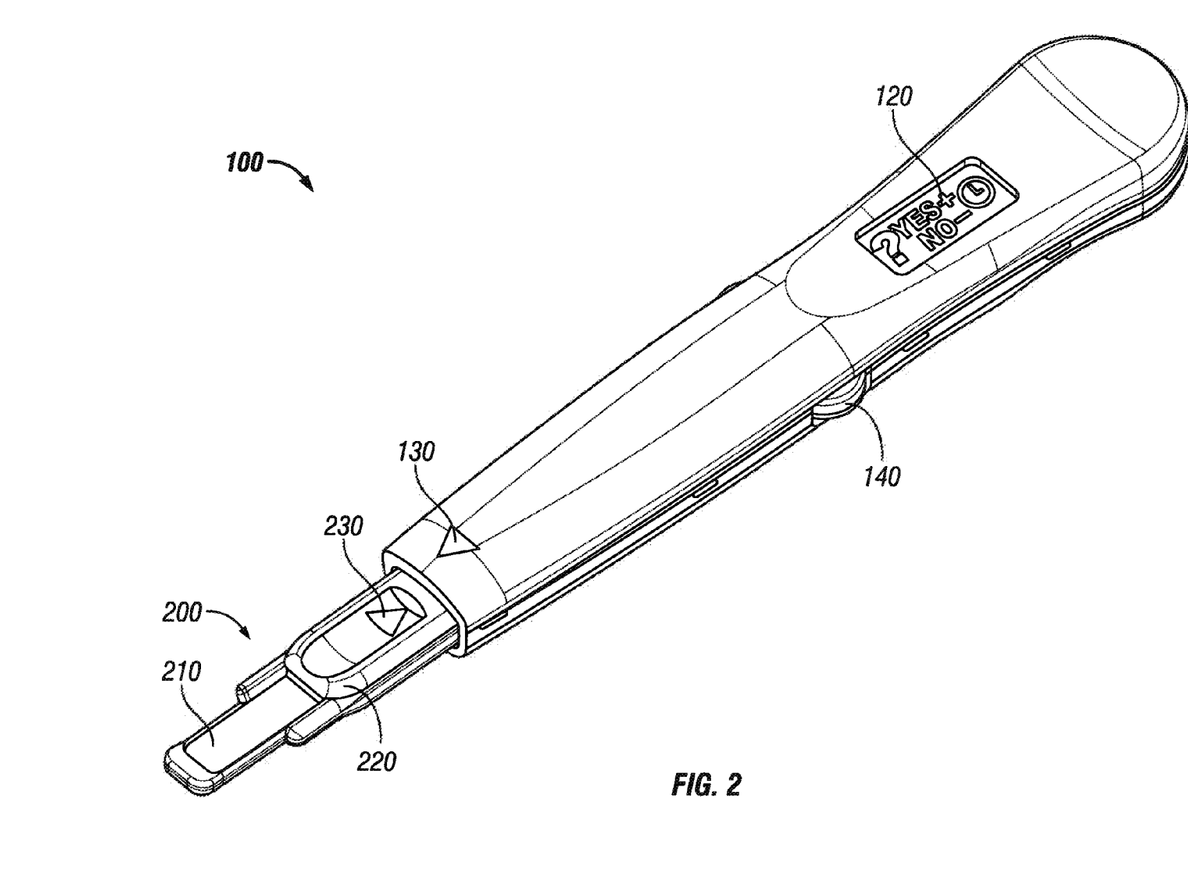
FIG. 2 is a top perspective view of an example of a reader device with a disposable test stick according to an implementation of the invention.

FIG. 2 is a top perspective view of the reader device of FIG. 1 with a test stick inserted. In the example shown, the device 100 is accepting a test stick assembly 200 housing the actual test strip 210. It is desirable for the test stick assembly 200 to couple with the device 100 so that the test stick assembly 200 will not fall out of the device 100 and may form a water resistant seal to protect a portion of the device 100 from fluid samples collected via the test stick assembly 200. The coupling should also minimize ambient light leakage into the device when testing is being performed on a test strip. Fluid samples collected via the test stick assembly 200 are generally urine, although depending on the test being performed, could be blood, sweat, tears, saliva, or any bodily fluid. An example test strip 210 will be described below in reference to FIG. 5. The test stick assembly includes a test stick housing 220. In an implementation, the test stick housing 220 may be formed from plastic. The test stick assembly 200 includes a test stick alignment marker 230 corresponding with the test stick alignment marker 130 on the device 100. The test stick assembly 200 may also include a clicking sound feature to indicate proper alignment and insertion into device 100.

Figure 3:
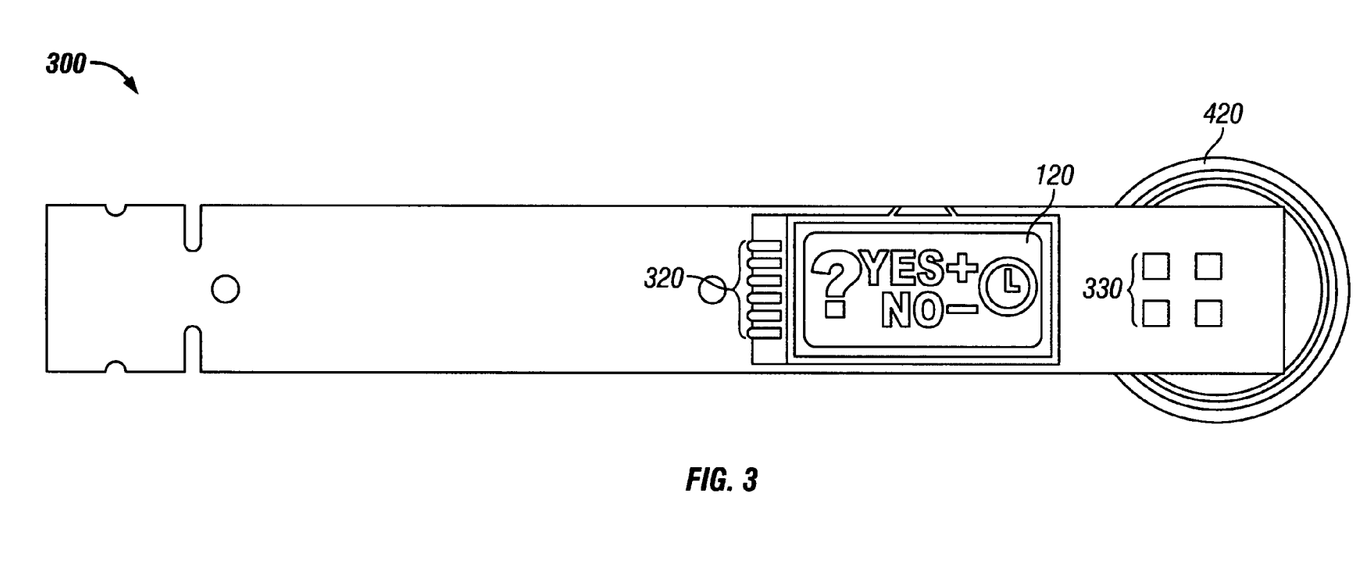
FIG. 3 is a top view of an example of a printed circuit board for a reader device according to an implementation of the invention.

FIG. 3 is a top view of a printed circuit board housed in the reader device of FIGS. 1 and 2. The display 120 is coupled with the printed circuit board 300 using one or more signal lines 320. The printed circuit board may include one or more input/output (I/O) terminals 330. The I/O terminals 330 may be used to read or write data from a memory (e.g., collected analyte readings, new program instructions, etc.).

Figure 4:
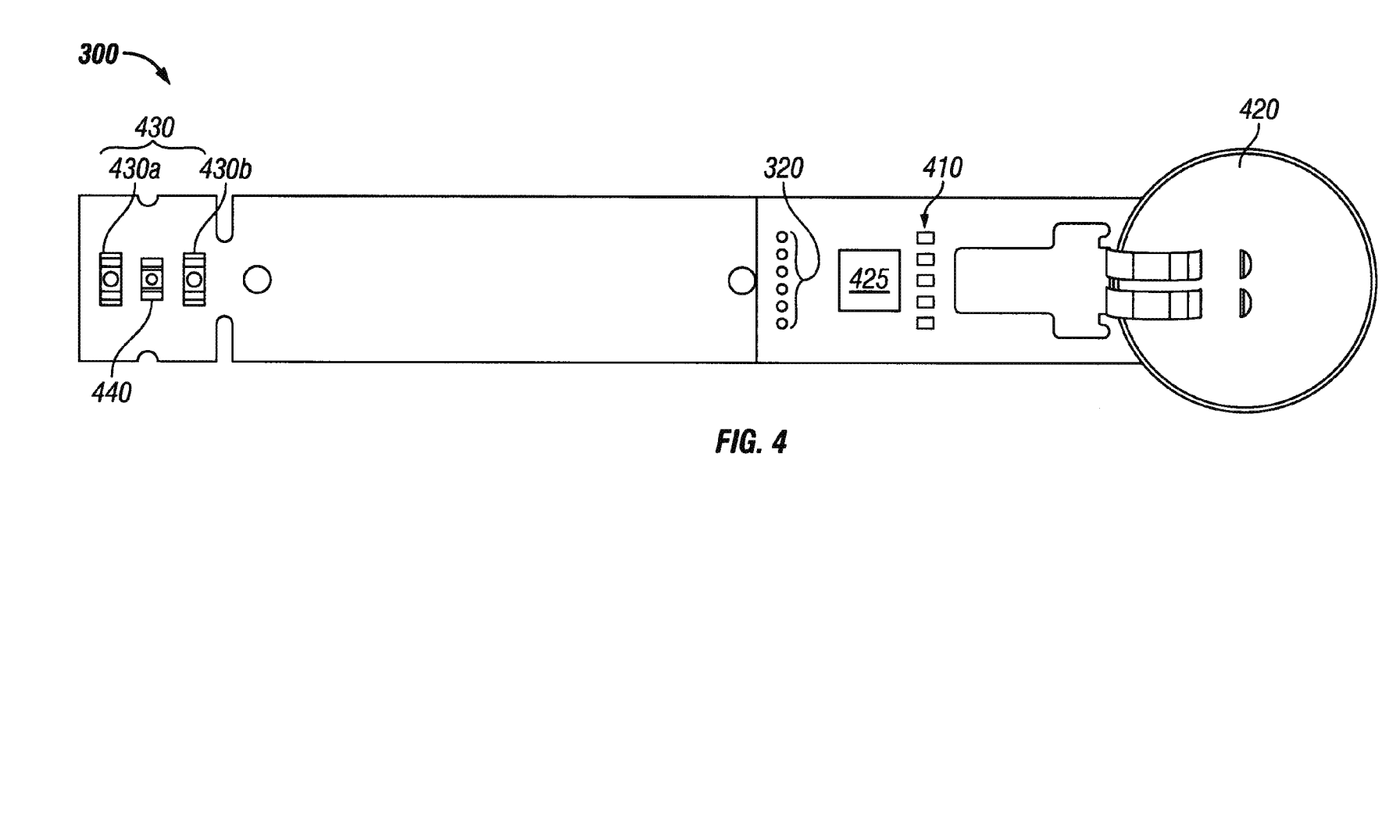
FIG. 4 is a bottom view of an example of a printed circuit board for a reader device according to an implementation of the invention.

FIG. 4 is a bottom view of the printed circuit board of FIG. 3. The printed circuit board 300 includes a processor/memory chip 425. The processor chip 425 is coupled with the display 120 and to one or more data I/O pads for test, data downloads, programming, etc. The memory may be used to store data received or produced by the processor chip 425. The memory may also be used to store instructions to direct operation of the processor chip 425. The printed circuit board 300 may further be coupled to a power source 420. In the example shown in FIG. 4, the power source is a battery, although any other suitable power source may be used. Discrete components such as resistors and capacitors 410 may also be provided on the printed circuit board 300.

The printed circuit board 300 includes one or more sensors 430. In the example shown in FIG. 4, the printed circuit board 300 includes two optical sensors 430a and 430b. In this implementation, the sensors 430 may be phototransistors. In other implementations, the sensors 430 may be one or more photodiodes, electroactive sensors or radioactivity sensors. The sensors may be of the same or different types. The sensors 430 are coupled with the processor chip 425.

The printed circuit board 300 may include an emitter 440. In an implementation including photoelectric sensors 430, the emitter 440 may be a light source such as a light emitting diode (LED). In an implementation including photoelectric sensors 430, as shown for example in FIG. 4, the light source 440 may be located equidistant between the photoelectric sensors 430a and 430b. The light source 440 may be coupled with the processor chip 425. The light source 440 may illuminate according to a configurable pattern. In an implementation where the light source 440 is coupled with the processor chip, the illumination pattern may be controlled by the processor chip 425. In an implementation where the light source 440 is not coupled with the processor chip 425, the illumination pattern may be controlled by a separate timing circuit.

As the emitter 440 illuminates the test strip 210, the sensor 430 may detect a response from the illumination. For example, in an implementation where the emitter 440 is a light source, the photoelectric sensor 430 will detect the amount of light reflected by the test strip 210. An example method of detection will be discussed in more detail below.

The emitter 440 and sensor 430 may be used to detect the insertion of a test stick. When the reader device is not assembled with a test stick, the emitter in the reader device can turn on periodically, for example, every two seconds. Detection of the presence of a test stick may be achieved by detecting a large difference in sensor response depending on whether the emitter is on or off due to the presence of the nearby reflective surface of the test stick. For example, in an implementation including two photodiode sensors, four readings may be captured: (1) first sensor output with emitter on, (2) first sensor output with emitter off, (3) second sensor output with emitter on, and (4) second sensor output with emitter off. In this example, very low and approximately equal readings for all four indicate that the reader device is still in the packaging or sitting on the counter waiting for the next test to be performed. Readings indicating a high light intensity at the photodectector for tests 1 and 3 and a low light intensity at the photodetector for tests 2 and 4 indicate the presence of a test stick 210. The device 100 may use this information to alter operation mode (e.g., from low power stand-by mode in the packaging to higher power test mode when a strip is inserted).

Figure 5:
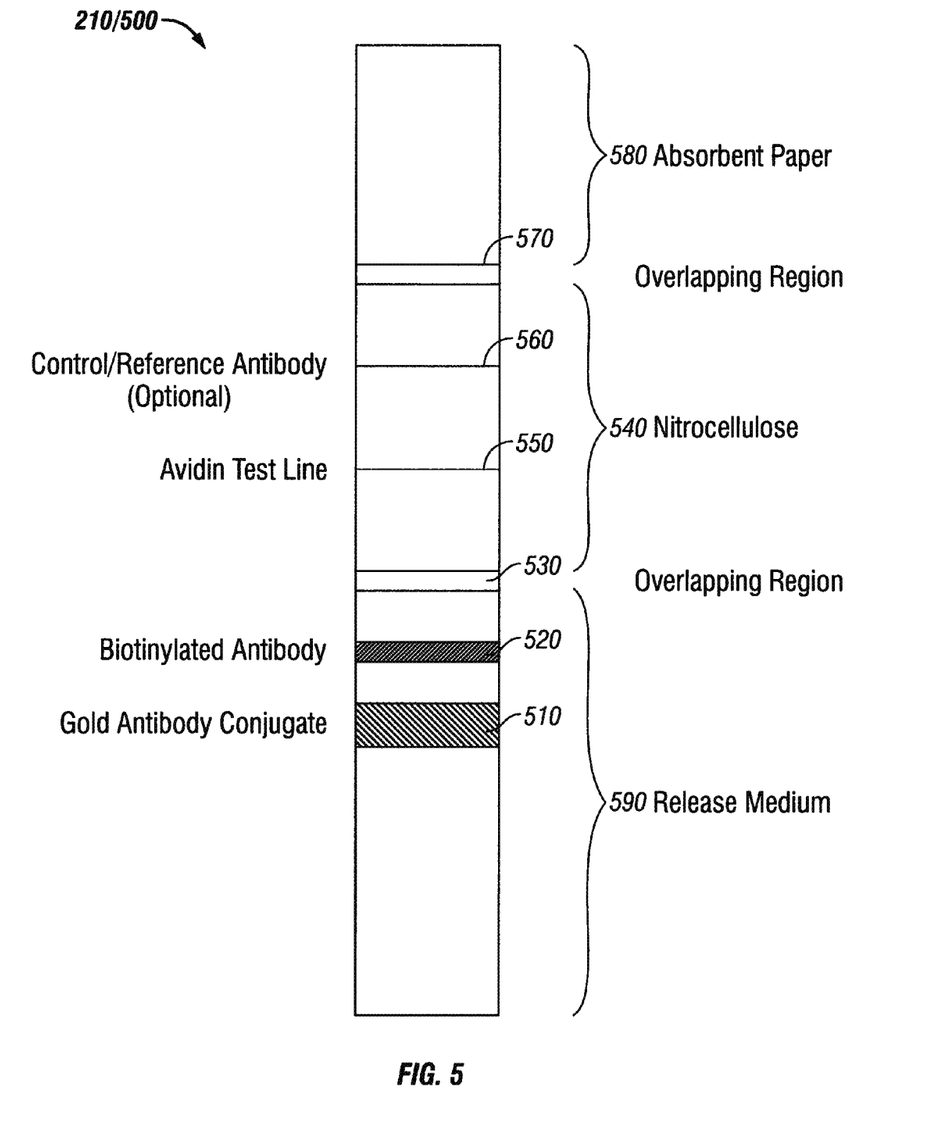
FIG. 5 is a diagram of an example of a triphasic test strip suitable for use in an implementation of the invention.

FIG. 5 is a diagram of an example of a triphasic test strip suitable for use in an implementation of the invention, although it will be appreciated that a wide variety of test strip designs may be used. The fluid path along the test strip 500 will be discussed starting with the bottom of the figure and moving up. It will be recognized that this spatial orientation is merely a convenience. At the bottom of the test strip 500, a fluid sample may be applied. The test strip 500 may be formed from an absorbent material to aid in the uptake of the fluid sample. The fluid sample may encounter a conjugate region 510. In the example shown, the conjugate region 510 is a colloidal gold antibody conjugate region where the antibody binds to the analyte of interest (e.g. LH). As the fluid sample passes through the conjugate region 510, analyte in the fluid sample will bind the gold conjugated antibody in the liquid phase and carry the conjugate-analyte complex along the strip. The fluid sample may then pass through a second antibody region 520. In the example shown, the second antibody region 520 includes biotinylated antibody that specifically binds to a different epitope on the analyte of interest than the gold conjugated antibody, forming a "sandwich" of analyte and two antibodies, one with colloidal gold, and the other with biotin. The sandwich may then be carried further along the test strip across a first overlapping region 530. The area from the start of the test strip 500 to the first overlapping region 530 may generally be referred to as the release medium 590.

After the overlapping region 530, the test strip 500 includes a nitrocellulose portion 540. As the fluid sample continues along the test strip 500, the sample next encounters a test line 550. In the example shown in FIG. 5, the test line 550 is an avidin test line for binding the biotin on the second antibody to trap the sandwich (with the gold) at the test line. The test line 550 will thus become darker as more of the sandwich complexes are accumulated. In an example implementation where the conjugate comprises colloidal gold, the electronics system, which may include sensors and/or a processor for performing a transformative algorithm on sensed data, may measure the colloidal gold specifically bound at the test line 550 of the test strip 500. After the test line 550, the test strip 500 may include a control line 560. The control line 560 may also generally be referred to as a reference line. When present, the control line 560 includes antibodies or other proteins that specifically bind the gold conjugated antibody to provide a measurement of gold bound antibody in the fluid that is not specifically bound to the analyte. Reflectance measurements from the test line 550 and/or control/reference line 560 may be used separately to define successful testing and analyte concentrations. In some embodiments, the reflectance of light from the test line 550 may be compared with the reflectance from the test strip downstream from the test line 550 in a region where there may or may not be a control/reference line 560 to define successful testing and analyte concentrations. Strips without a control/reference line may be advantageous because it eliminates the need for the antibodies at this line, reducing cost of the strip.

The nitrocellulose portion 540 may terminate with a second overlapping region 570. The second overlapping region 570 may serve as a border between the nitrocellulose portion 540 and an absorbent portion 580 of the test strip. The absorbent portion 580 of the test strip 500 facilitates the uptake of the fluid sample as it arrives at the end of the test strip 500.

Test strips of this nature are known in the art, and are described in more detail in, for example, FIGS. 2-6 and the accompanying description of U.S. Pat. No. 6,319,676, the entire content of which is hereby incorporated by reference.

It may be desirable to align the test strip 500 when inserted into the device 100 such that the nitrocellulous region is substantially located under the sensor 430. A first sensor 430 may be located directly over the test line 550. A second sensor may be located directly over a second region of the strip that may or may not contain a control line. Further details of one embodiment of a sensor 430, emitter 440, and test strip 500 alignment are discussed below. Measurements of the reflectivities provide a measure of analyte concentration.

Figure 6:
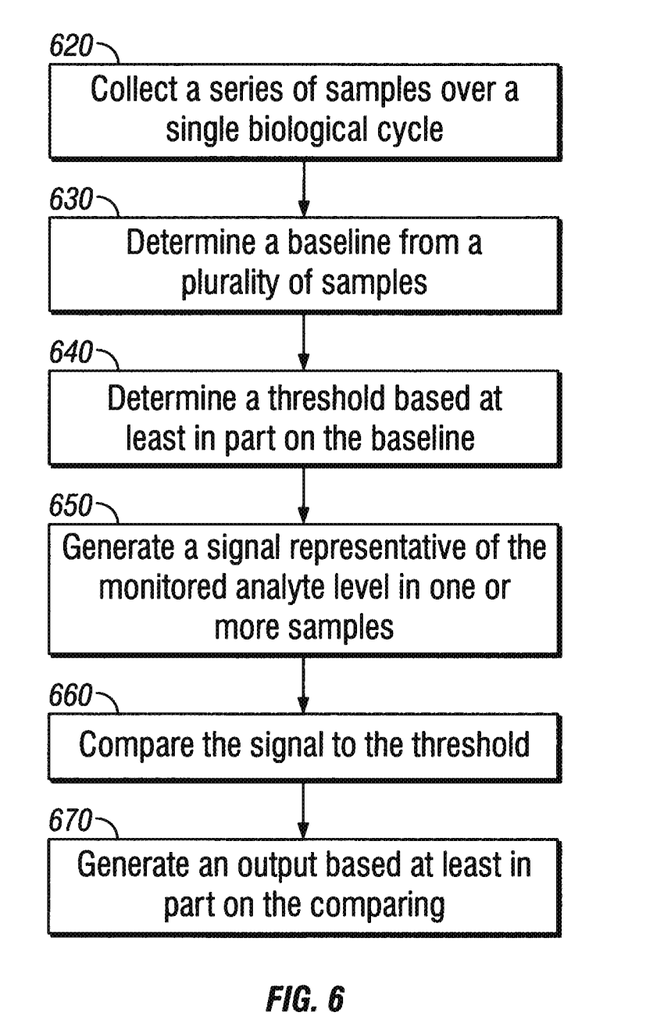
FIG. 6 is a flow diagram of an example of an implementation of the method for detecting a variation in a monitored analyte level in a fluid sample from an individual.

Turning now to analyte change detection methods which may be used by the device, FIG. 6 is a flow diagram of an example of an implementation of the method for detecting a variation in a monitored analyte level in a fluid sample from an individual. At a block 620, a series of samples may be collected. The samples collected may be, for example, urine samples. Preferably, the series of samples is collected over a single biological cycle of the user, for example, over a single menstrual cycle. This allows a baseline and threshold to be developed in the same cycle. At a block 630, a baseline may be determined from a plurality of samples of the series collected. The baseline samples may be initial samples collected over an initial plurality of days of the cycle. For example, samples collected on the first three days after a user's menses may be used to determine a baseline. In an implementation, the samples may be collected on any one or more of the third through the tenth day from the onset of menses of a menstrual cycle of the individual.

At a block 640, a threshold may be associated with the monitored analyte level for the individual based at least in part on the determined baseline. The threshold represents a personalized value for the specific individual monitoring the analyte level for a current biological status rather than relying on previously measured cycle information or a fixed threshold for all individuals. An example of one possible determination of a baseline and threshold will be described in further detail below in reference to FIG. 7.

At a block 650, a signal may be generated representative of the monitored analyte level in one or more samples. For example, the signal may be based at least in part on an amount of light reflected by the test line on the test strip.

At a block 660, the signal may be compared to the threshold. The comparison may include detection of a difference between the values and/or statistical or probability analyses of the values. At a block 670, an output may be generated based at least in part on the comparing. In the case where the signal value exceeds the threshold value, the amount of measured analyte may be higher in the current sample under test than the threshold value. In an implementation where the analyte is (LH), this condition may correspond with an LH surge for the individual thereby predicting the onset of ovulation. It will be appreciated that the method may also detect the inverse case and output a signal if the signal value for the selected sample falls below the threshold value. For example, in the case where the measured analyte is glucose, it may be desirable to produce an output at block 670 indicating that the measured level falls below the threshold thereby indicating a low blood sugar level. Furthermore, in a competitive assay, for example, a higher analyte concentration may correspond to a signal value that drops below a threshold.

In some implementations, the process may include a disable step. In the case where LH is the monitored analyte, the process may terminate once an LH surge is detected and a signal indicating the same transmitted, for example, to a display. In an implementation, the disabling may be based on the number of samples collected. For example, once the process has collected 20 samples, the process may terminate and the reader device disabled.

Figure 7:
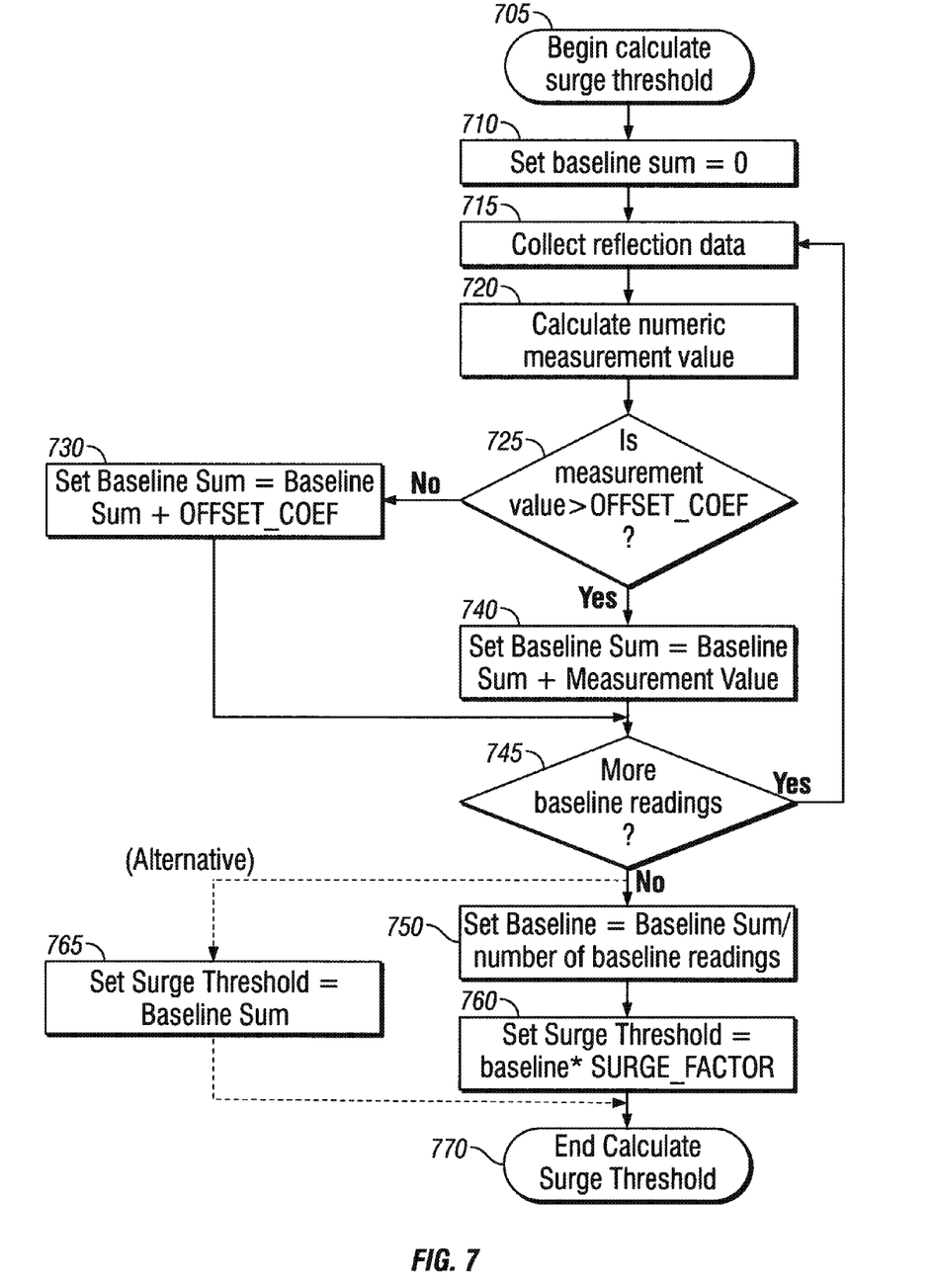
FIG. 7 is a flow diagram of an example of the surge threshold calculation according to an implementation of the invention.

FIG. 7 is a flow diagram of an example of an implementation of the surge threshold calculation according to an implementation of the invention. The calculation begins at a block 705. At a block 710, the baseline sum is set to a value of zero. At a block 715, sensor data is collected. In an implementation where the sensor is a photoelectric sensor, the data collected is a measure of the amount of light reflected. At a block 720, the sensor data collected at block 715 is used to calculate a numeric measurement value. At a decision block 725, the calculated numeric measurement value is compared to an offset coefficient. If the measurement value is less than the offset coefficient, then the flow continues to a block 730. At block 730, since the measurement value is less than the offset coefficient, the flow sets the value at a predetermined minimum, the offset coefficient. At block 730 the baseline sum is set to the previous baseline sum plus the offset coefficient. If the measurement value is greater than the offset coefficient, then the flow continues to a block 740. At block 740, the baseline sum is set equal to the previous baseline sum plus the measurement value. After block 730 or 740, the flow continues to decision block 745. At block 745, the flow determines if more readings should be collected. For example, the device may be configured to collect three baseline readings, one per day on each of the first three days after a user's menses. If more baseline readings are needed, the flow returns to block 715. If no additional baseline readings are needed, the flow continues to a block 750. To a user of the device, a baseline collection versus an analysis collection may be indistinguishable.

Once the baseline readings have been collected, block 750 sets the baseline equal to the baseline sum divided by the number of baseline readings collected. This provides an average reading based on the number of baseline days. It will be appreciated that other calculation methods such as a weighted average, moving average, or calculation methods taking into account other variables such as user's age, number of children, height, or weight may be used to calculate the baseline. The flow continues to a block 760 where the surge threshold is set to the baseline multiplied by a surge factor. For example, in an implementation, a surge factor of three may be desirable. Depending on the monitored analyte, the surge factor may be configured to different values. For example, in an LH configuration, the surge factor may be three, while in a progesterone configuration the multiplier may be two.

In an implementation where the surge factor is equal to the number of baseline readings, the flow may take an alternative path after block 745. In this alternative path, at a block 765 the surge threshold is set to the sum of the baseline readings. In this specific case, the surge factor times the average baseline reading may be the same as the sum of the baseline readings. In some cases, this can reduce the number of computations required.

The flow ends at a block 770 with a calculated surge threshold. The flow may be implemented as a hardware circuit or as instructions executed by the processor chip. The calculated surge threshold may be stored by the device, for example in memory coupled with or present in the processor chip. In this example, the threshold value calculated at the beginning of a cycle is used to monitor and detect variations during the same cycle.

Figure 8:
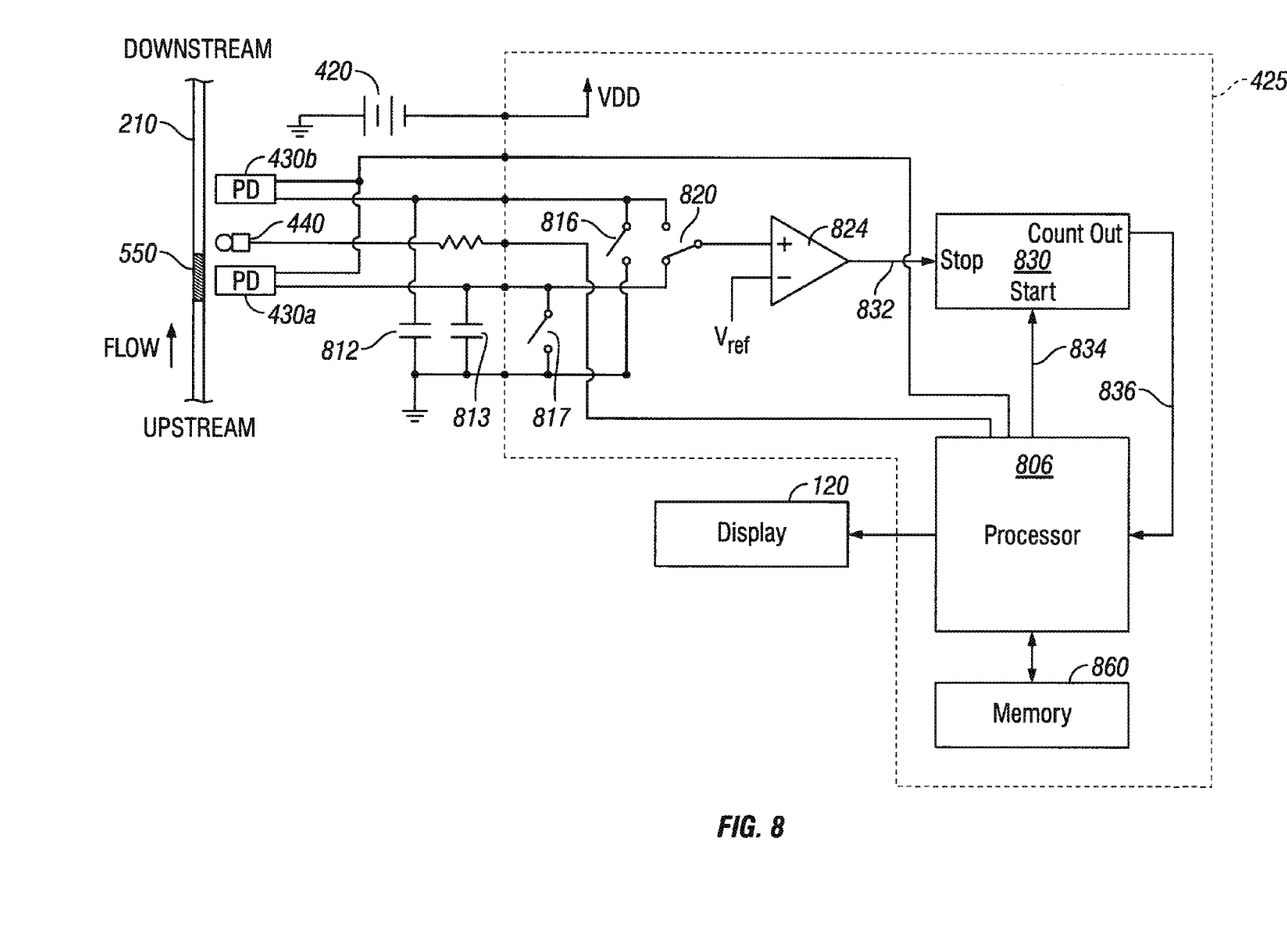
FIG. 8 is a circuit diagram of an example circuit suitable for use in an implementation of the invention.

FIG. 8 is a circuit diagram of a circuit suitable for use in an implementation of the invention. This implementation includes photodetectors 403a and 403b as the sensors. Sensor 430a may be positioned substantially over the test line 550 of the test strip. Sensor 430b many be positioned over a blank region downstream of the test line on the strip. In this embodiment, no control/reference line is present. As described further below, reflectance measurements are made for these two regions for a time period after a fluid sample is applied to one end of the strip.

The circuit includes a light emitter 440. The light emitter 440 may be an LED. The light emitter 440 is connected a processing/control circuit 806 that may be in the integrated circuit 425. The photodetectors 430a and 430b are also each coupled to the processing/control circuit 806 to control initiation of the photodetector operation. The output of photodetector 430a is coupled to capacitor 813, and the output of photodetector 430b is coupled to capacitor 812. The other side of each capacitor is grounded. Each capacitor further has a reset switch 817 and 816 connected across it to selectively discharge the capacitors. In operation, each photodetector output will charge its respective capacitor with its output current. The time required to charge each capacitor to a defined threshold level is a measure of the photodetector output, and thus is a measure of the reflectivity of the strip in the region under each photodetector.

The time period to charge the capacitor to the threshold may be determined as follows. If photodetector 430a is being measured, LED 440 is switched on, switch 817 is opened, a counter 830 is started, and a switch 820 is used to connect the high side of capacitor 813 to the positive input of a comparator 824. The negative input to the comparator 824 is coupled to a reference voltage, which is advantageously derived from the battery voltage VDD. For example, the reference voltage may be ½ of VDD. The output 832 of the comparator 824 is coupled to a stop input of the counter 830 that stops the counter 830 when the comparator output goes high. As capacitor 813 is charged by the photodetector 430a output, the voltage on the high side of capacitor 813 increases, increasing the voltage input to the positive input of the comparator 824. When this voltage reaches the reference voltage input to the negative side of the comparator 824, the comparator output 832 transitions from low to high. The count value 836, which is a measure of the time between counter start at the beginning of the process and counter stop when the comparator goes high, is fed to the processor 806. In this embodiment, a larger count indicates a longer time for capacitor charging, indicating a lower photodetector output, and therefore a less reflective surface under the photodetector. Once a count for photodetector 430a is acquired, the switch 817 is closed, and the process repeats for photodetector 430b, switch 816, and capacitor 812, with the switch 820 in the other position.

Collectively, the elements of the processor chip 425 are connected to one side of a power supply 420. Explicit power transmission traces between the elements of the processor chip 425 have been omitted from FIG. 8. The other side of the power supply 420 is connected to a ground. Integrated circuit 425 may also include a memory 860 for storing data and instructions as described above.

In operation, the reader 100 detects that a test strip is installed and begins taking count values for photodetector 430a (the upstream photodetector) and 430b (the downstream photodetector) at a polling rate. A rate of once per second for the polling rate has been found suitable for reasons that will be described further below. From each pair of counts, the reader computes a measurement value M defined as follows:

$$M=S*((A/B)-(C/D)) \qquad \text{Equation 1}$$

Where A=initial downstream count value
B=current downstream count value
C=initial upstream count value
D=current upstream count value
S=constant scale factor In use of the device, immediately following test strip installation and application of a sample, the value of M is near zero, because both areas of the strip under each photodetector have approximately equal reflectances before the sample migrates down the strip to reach the photodetector regions. Furthermore, the current counts B and D will be about equal to the initial counts A and C, making M about equal to 1-1 which is near zero. When the fluid front of the sample first reaches the upstream detector, the count value D will increase because the strip in that region becomes less reflective, causing M to increase since A/B is still near 1, but C/D is now less than 1. The reconstituted gold labeled antibodies and antibody-antigen sandwiches slightly lag the fluid front. When the gold reaches the region under the upstream photodetector, D increases further, which further increases the value for M. If antigen is present in the sample, gold labeled antibody-antigen sandwiches will be captured at the test line 550, stopping their further migration down the strip. When the fluid front and gold labeled antibodies reach the downstream photodetector region, this area will darken also, increasing the count value of B, which decreases the value for M, because A/B becomes smaller than 1. As the assay develops further, most of the gold labeled antibodies that are not part of sandwich complexes and are thus not captured at the test line 550 migrate past the downstream detector region, leaving behind a residual background. After a few minutes, the values for B and D stabilize, stabilizing the value for M to a final value. This value for M will be greater than 0 if the reflectance of the test line is lower than the reflectance of the blank region, which indicates that gold labeled antibody-antigen sandwiches captured at the test line 550 exceed the residual background of gold labeled antibodies in the blank downstream region of the strip (because D will be larger than B). Higher final values of M indicate higher concentrations of antigen (e.g. LH) in the sample.

As described above, the reader does not monitor M as a continuous variable, but rather generates M values at a given polling rate, which may be once per second. Sampled values of M may be handled as follows. The first pair of collected counts are used for initial values of A and C, and no value for M is computed. The next pair of samples are used for B and D, which are combined with the A and C counts to produce a value for M. The reader waits for up to 10 minutes (600 samples) for the value of M to exceed a fluid detection threshold. At some points during this phase, the values of A and C may be replaced with B and D as long as the value of M is less than a small threshold, typically a few counts. This can be used to compensate for drift in the battery, led, and sensors. When the value of M exceeds the fluid detection threshold, this indicates that for this most recent pair of counts, the fluid front has reached the upstream detector and D has become significantly larger. If the value for M does not exceed the fluid detection threshold for 10 minutes (e.g. for 600 samples) the assay may be aborted and an error signal may be displayed. Typically, M will exceed the fluid detection threshold within a minute after sample application, but a user may delay sample application after installation of the test stick which is when sampling is automatically initiated.

Once the computed value for M exceeds the fluid detection threshold, the values for A and C can no longer be reset and are used for all further M computations. Once the fluid detection threshold is exceeded, the reader continues to compute M at each polling time, and will generally detect a continually increasing value for M. Because the gold will now tend to quickly increase the D count value, the reader monitors M to determine if M passes a second, higher threshold. In one embodiment, the reader detects whether M passes the second threshold within seven seconds (e.g. within seven samples) of the sample at which M exceeded the fluid detection threshold. If the value for M does not exceed the second threshold within this time the assay may be aborted and an error signal may be displayed.

Once the value for M exceeds the second threshold, indicating that the assay is proceeding correctly, the system may continue taking samples for an additional five minutes (e.g. 300 more samples) and use the final count values at this end point for a final value of M that indicates antigen concentration. These final values for M can be used as described above in FIG. 7 to compute a surge threshold (e.g. the surge threshold equals the sum of final M values for the first, second, and third assays). Subsequently, the final M for each assay can be compared to this surge threshold to detect a surge in antigen concentration and provide an output to the user indicating the presence of the surge. In this embodiment, the "measurement value" of FIG. 7 is an M value from Equation 1.

The actual numerical values for M that are produced with this algorithm will depend on the value selected for the scale factor S and the sensitivity of the assay materials. In one embodiment developed by the applicants, the scale factor is 666, and the resulting M values generally range from relatively small negative numbers to 100 or so. In this embodiment, the fluid detection threshold may be 20, and the second threshold may be 85.

It will be appreciated that a variety of alternative and additional algorithms can be used to process count values. For example, it would be possible to assume the assay was performed correctly, and only sample a count pair upon strip insertion to produce an A and B, wait 10 or 15 minutes, and produce a second count pair for B and D, and use the resulting M from equation 1 as the assay result. As additions to the above described method, the individual count values can be used to detect additional aspects of successful or failed assays. For example, changes in M can be correlated to individual changes in B and/or D to ensure that the changes in M are being caused by changes in B and D that are expected at that point in the assay. Absolute values for the counts can also be used to detect operational errors with the photodetectors or light source. Count values or M values could also be processed using averaging or other statistical methods to reduce noise or enhance certain signal characteristics that are desired to be detected.

The polling rate may also be changed. With the above algorithm, if the polling rate is very high, battery life is reduced. On the other hand, if the sampling rate is too low, the changes in M produced as the fluid front crosses the first and second detector regions could be detected late or missed entirely. As noted above, a sampling rate of once per second has been found suitable.

As another enhancement, M values can be analyzed to detect early LH outlier readings. For example, if the first three M values are 4, 35, and 6, then the 35 can be discarded as an outlier, and the next computed M value can be used in the baseline computation. Also, if the first few M values are all very large, such as 50 or 75 or more, the reader can display an error code indicating the user should not perform further assays in that cycle, assuming that the user did not start the test early in the cycle, and perhaps was in the midst of a surge when testing began.

To test the accuracy of the above described device, urine samples were collected from test subjects. The urine samples were tested for LH concentration with a Siemens Immulite 1000 analyzer to produce actual LH concentration values. The same urine samples were also applied to the device described above, and also to the analog "color matching" ovulation detector commercially available as the First Response® Daily Ovulation Test. The results are presented in the tables below:

Subject 1:

| Day of Cycle | Immulite Results (mIU/ml) | Invention Embodiment Display Output | First Response ® Device Visual Results |
|---|---|---|---|
| 5 | 21 | NO– | Negative |
| 6 | 30 | NO– | Negative |
| 7 | 42 | NO– | Negative |
| 8 | 45 | NO– | Negative |
| 9 | 44 | NO– | Negative |
| 10 | 28 | NO– | Negative |
| 11 | 63 | NO– | Negative |
| 12 | 23 | NO– | Negative |
| 13 | 43 | NO– | Negative |
| 14 | 143 | YES+ | Negative |
| 15 | 173 | | Positive |

Subject 2:

| Day of Cycle | Immulite Results (mIU/ml) | Invention Embodiment Display Output | First Response ® Device Visual Results |
|---|---|---|---|
| 5 | 13 | NO– | Negative |
| 6 | 21 | NO– | Negative |
| 7 | 18 | NO– | Negative |
| 8 | 40 | NO– | Negative |
| 9 | 15 | NO– | Negative |
| 10 | 19 | NO– | Negative |
| 11 | 40 | NO– | Negative |
| 12 | 18 | NO– | Negative |
| 13 | 26 | NO– | Negative |

-continued

Subject 2:

| Day of Cycle | Immulite Results (mIU/ml) | Invention Embodiment Display Output | First Response ® Device Visual Results |
|---|---|---|---|
| 14 | 28 | NO– | Negative |
| 15 | 53 | YES+ | Negative |
| 16 | 181 | | Positive |

Subject 3:

| Day of Cycle | Immulite Results (mIU/ml) | Invention Embodiment Display Output | First Response ® Device Visual Results |
|---|---|---|---|
| 5 | 5 | NO– | Negative |
| 6 | 6 | NO– | Negative |
| 7 | 7 | NO– | Negative |
| 8 | 5 | NO– | Negative |
| 9 | 7 | NO– | Negative |
| 10 | 6 | NO– | Negative |
| 11 | 5 | NO– | Negative |
| 12 | 6 | NO– | Negative |
| 13 | 11 | NO– | Negative |
| 14 | 65 | YES+ | Positive |

The above examples illustrate the varying levels of baseline LH concentration in different subjects. Furthermore, it can be seen that for women with an existing elevated level of LH, e.g. more than about 20 mIU/ml early in the menstrual cycle, the invention embodiment reader predicts the LH surge a day earlier than the analog First Response® prior art product. This can be attributed to the use of a personalized baseline as described above. This single day of advance detection is significant, and can mean the difference between a pregnancy or no pregnancy in a given cycle.

It will be appreciated that the above described system could be used to detect analytes other than hormones, with especially advantageous application in any environment where samples are collected, and the diagnostic test may be interpreted according to a photosensitive reading. For example, variation of the monitored analyte may be used to indicate an onset of menopause (e.g., natural menopause, perimenopause, induced menopause, premature menopause, or post menopause) or ovarian reserve for the individual. In an implementation, variation of a monitored analyte such as progesterone may be used to indicate an onset of an abnormal pregnancy (e.g., failed implantation, ectopic pregnancy) for the individual. In an example progesterone implementation, a normal pregnancy is detected if the progesterone level is greater than the threshold value while levels equal to or less than the threshold indicate an abnormal pregnancy. The detection method or device may be included in a test kit such as an ovulation detector test kit sensing LH in urine samples from an individual.

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

As used herein, a phrase referring to a list of items refers to any combination of those items, including single members. As an example, "at least one of: a, b, or c" is intended to cover: a, b, c, a-b, a-c, b-c, and a-b-c.

The various operations of methods described above may be performed by any suitable means capable of performing the operations, such as various hardware and/or software component(s), circuits, and/or module(s). Generally, any operations illustrated in the Figures may be performed by corresponding functional means capable of performing the operations.

The various illustrative logical blocks, modules and circuits described in connection with the present disclosure may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

In one or more aspects, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a web-site, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Thus, in some aspects computer readable medium may comprise non-transitory computer readable medium (e.g., tangible media). In addition, in some aspects computer readable medium may comprise transitory computer readable medium (e.g., a signal). Combinations of the above should also be included within the scope of computer-readable media.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

Thus, certain aspects may comprise a computer program product for performing the operations presented herein. For example, such a computer program product may comprise a computer readable medium having instructions stored (and/or encoded) thereon, the instructions being executable by one or more processors to perform the operations described herein. For certain aspects, the computer program product may include packaging material.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc, or floppy disk, etc.), such that a user terminal and/or base station can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the disclosure.

While the foregoing is directed to aspects of the present disclosure, other and further aspects of the disclosure may be devised without departing from the basic scope thereof.

What is claimed is:

1. A method of using a test strip reader to detect a variation in a monitored analyte level in a fluid sample from an individual, the method comprising:
   (i) contacting the fluid sample from the individual with a test strip associated with the test strip reader, wherein the test strip reader is configured to receive a plurality of test strips and wherein the test strip reader comprises one or more sensors;
   (ii) detecting, via the one or more sensors, an analyte concentration within the test strip reader to generate a sample value;
   (iii) storing the sample value;
   (iv) repeating steps (i)-(iii) a corresponding series of times using the plurality of test strips over a plurality of days during a single biological cycle of the individual to generate a plurality of stored sample values;
   (v) generating a set of baseline values from the plurality of stored sample values via processing circuitry in the test strip reader, wherein the processing circuitry determines the set of baseline values by discarding a sample value that is identified as an outlier, and substituting the discarded sample value with a constant or with a later acquired sample value, wherein the set of baseline values is generated from fluid samples obtained during the first three days or any one or more of the third through tenth days from onset of menses of a menstrual cycle of the individual;
   (vi) generating, via the processing circuitry, a personal threshold level associated with the monitored analyte level for the individual based at least in part on the set of baseline values;
   (vii) generating via the one or more sensors a signal representative of the monitored analyte level in one or more samples in the series;
   (viii) comparing via the processing circuitry the signal to the personal threshold level; and
   (ix) generating an output based at least in part on a result of the comparing.

2. The method of claim 1, wherein the monitored analyte is a hormone or hormone metabolite.

3. The method of claim 1, wherein the monitored analyte is selected from a group comprising follicle stimulating hormone, thyroid stimulating hormone, luteinizing hormone, human chorionic gonadotropin, estrogen, progesterone, testosterone, or metabolites thereof.

4. The method of claim 1, wherein the fluid sample is urine.

5. The method of claim 1, wherein generating a signal representative of the monitored analyte level comprises analyzing a test strip.

6. The method of claim 1, wherein the signal representative of the monitored analyte level comprises a photometric or an electroactive signal.

7. The method of claim 1, wherein the set of baseline values is generated from at least some fluid samples obtained on any one or more of the third through the tenth day from the onset of menses of a menstrual cycle of the individual.

8. The method of claim 1, wherein the set of baseline values is generated from fluid samples obtained after cessation of menses of a menstrual cycle of the individual.

9. The method of claim 1, wherein the threshold is an average of the set of baseline values times a surge factor.

10. The method of claim 9, wherein the surge factor is three.

11. The method of claim 1, wherein the threshold is greater than an average of the set of baseline values.

12. The method of claim 1, wherein the threshold is less than an average of the set of baseline values.

13. The method of claim 1, wherein the set of baseline values is derived from monitored analyte level data from a biological cycle in which the variation is to be detected.

14. The method of claim 13, wherein the variation indicates an onset of a menstrual cycle ovulatory phase for the individual.

15. The method of claim 13, wherein the monitored analyte is luteinizing hormone.

16. The method of claim 13, wherein the monitored analyte is progesterone.

17. The method of claim 1, wherein comparing the signal comprises comparing the signal to a configurable signal range.

18. The method of claim 1, further comprising disabling the test strip reader based at least in part on the result.

* * * * *